United States Patent [19]

Aoe et al.

[11] Patent Number: 5,112,964
[45] Date of Patent: May 12, 1992

[54] WATER-SOLUBLE HEMICELLULOSE

[75] Inventors: Seiichiro Aoe; Taishi Oda, both of Kawagoe; Masanori Nakaoka, Nagareyama; Seiji Kurosawa, Sayama, all of Japan

[73] Assignee: Snow Brand Milk Products Co., Ltd., Sapporo, Japan

[21] Appl. No.: 442,656

[22] Filed: Nov. 29, 1989

[30] Foreign Application Priority Data

Dec. 7, 1988 [JP] Japan .................................. 63-307719
Aug. 10, 1989 [JP] Japan .................................. 1-205697

[51] Int. Cl.⁵ ............................................. C08B 15/08
[52] U.S. Cl. ...................................... 536/56; 536/127; 536/128

[58] Field of Search ........................... 536/56, 127, 128

[56] References Cited

U.S. PATENT DOCUMENTS 4,038,481  7/1977  Antrim et al. ......................... 536/56

Primary Examiner—Nathan M. Nutter
Assistant Examiner—Jeffrey Culpeper Mullis
Attorney, Agent, or Firm—Fleit, Jacobson, Cohn, Price, Holman & Stern

[57] ABSTRACT

The present invention provides a process of producing a water-soluble hemicellulose comprising a starch removing stage, an extraction stage and a neutralization and desalting stage and the use of the obtained water-soluble hemicellulose as a health food.

8 Claims, No Drawings

WATER-SOLUBLE HEMICELLULOSE

BACKGROUND OF THE INVENTION

The present invention relates to a process of producing a water-soluble hemicellulose, in which the B fraction of hemicelluloses contained in rice bran, wheat bran or grain husk and having various kinds of physiological effect is extracted and separated from the bran or the husk, and to the use of water-soluble hemicellulose.

Cellulose, hemicelluloses, pectic substances, lignin, chitin, mucilages (galactomannan, glucomannan and the like), algal polysaccharides, chemically modified polysaccharides (chemically modified starch, carboxymethylcellulose and the like), etc. are designated as dietary fibers, and they are indigestible constituents which are contained in food and indigestible in human digestive enzymes. Recently, it is noted that the ingestion of these dietary fibers shows physiological effects. These dietary fibers are classified into water-soluble fibers and water-insoluble fibers.

It is reported that the water-soluble dietary fibers have the following advantages: 1) the fibers prevent the absorption of toxic substances or carcinogens present in the intestines and the fibers are excreted with these materials, 2) cholesterol, bile acids and heavy metals adhere to the fibers and these are excreted, and 3) the intestinal surroundings are improved by useful bacterias which are predominantly present in the intestinal micro flora. The insoluble fibers have the following advantages: 1) the fibers stimulate the motility of the large bowel and accelerate large bowel transit in spite of the slower transit time through the stomach and small intestine, and 2) the fecal water content and fecal weight are increased.

The B fraction of hemicelluloses which is a kind of water-soluble fibers has been studied because it has various kinds of physiological effect. A fractionation procedure of the hemicellulose, B fraction has been reported by Southgate, D. A. T. "The Chemistry of Dietary Fiber" in "Fiber in Human Nutrition", edited by Spiller, G. A. and Amen, R. J., pp31, Plenum Press, NY (1976), since then, several fractionation procedures of the hemicellulose B fraction have been reported (Japanese Patent Publication Numbers 59-1687, 59-1688 and 59-1689, Japanese Laid-Open Patent Publication Number 60-27365). However, the procedure of industrial mass production of hemicellulose B is yet unknown. As the reason, it is considered that each process cost much money and is time-consuming.

A food which is obtained by adding fibers is described in Japan Laid-Open Patent Application No. 58-187745. The food is obtained by adding fibers to processed food such as, for example, soy-bean paste, bean-curd, retort foods, pies or bread. The addition aims to obtain characteristics of resistance to age, prevention of water-staining, prevention of concretion, viscosity control, prevention of oil separation and the like. The addition does not aim to obtain food containing the hemicellulose B fraction for the main ingredients. The food contains only a little hemicellulose B fraction which has physiological useful effects. Accordingly, the physiological effect of the hemicellulose B fraction is not noticed in the above application.

In Japanese Laid-Open Patent Application No. 57-21324, it is described that hemicellulose which is extracted in alkaline solution from corn fibers inhibits hypercholesterolemia. However, the present invention is different from the above application, because the obtained hemicellulose in the present invention is separated and extracted from rice bran, wheat bran or grain husk which has effect in the most preferable conditions suitable for drinks and milk powder.

In Japanese Laid-Open Patent Application No. 63-165325, a kind of medicine for intestinal disorders which contains hemicellulose B fraction as an effective ingredient is disclosed. In the separation and extraction process, the removal of protein by using trichloroacetic acid and the purification by using ethanol precipitation are required, and the process is complicated.

In the U.S.A., milk powder in which fiber is mixed in the form of microcrystalline cellulose (MCC) for improving the property of is commercially available. However, since the MCC is a semi-synthesized product compound, its texture is bad. When the MCC was mixed with milk powder and dissolved in water, coagulation of colloids occurs. When it is added to drinks, the obtained drinks taste bad. Moreover, since the cellulose is a food fiber insoluble in water, it is impossible to expect the physiological effects which the above water-soluble food fiber have.

In Japanese Laid-Open Patent Application No. 61-24251, a low-caloric powder obtained by powdering the mixture of milk powder, beer yeast for food, saccharide which is not absorbed in the intestines and fibers is disclosed. The fibers described in the above invention are psylliun, pectin, guar gum and carrageenan. These fibers are slightly soluble in water and/or have high viscosity, so that when these fibers are added to milk powder, the treatment is troublesome and the obtained drinks containing the food fibers have bad texture.

SUMMARY OF THE INVENTION

The present invention has an object to provide a process in which the hemicellulose B fraction contained in rice bran, wheat bran or grain husk and having various kinds of physiological effect can be produced industrially and efficiently. Moreover, the hemicellulose B fraction in the present invention is added to foods such as yogurt, processed cheese, spread, cookies, sablé, ices, bread, puffed snacks and a medicine for constipation and the like, and can be used for healthy foods.

The present invention provides a process of producing a water-soluble hemicellulose comprising a starch removing stage for treating raw material of rice bran, wheat bran or grain husk in which a thermostable amylase is added to the raw material in the presence of hot water and the starch dissolved in the water is removed, an extraction stage in which the starch-free material is extracted under alkaline or acidic conditions with a solution, and a neutralization and desalting stage in which the obtained liquid containing the hemicellulose B fraction is neutralized and desalted to obtain the said water-soluble hemicellulose.

Apparatus and the other elements which are used in other fields can be used in each stage of the process of the present invention. The apparatus introducible in the series of the preparation stages can be used to obtain the water-soluble hemicellulose efficiently.

DETAILED DESCRIPTION OF THE INVENTION

In the starch removing stage, raw material is treated by adding a thermostable amylase in the presence of hot water (preferably at 70° C. or more) by means of a homomixer or a colloid mill and starch is homogenized and gelatinized. The thermostable amylase functions to accelerate the gelatinization of the starch and to shorten the process time.

In the extraction stage, when the starch-free material is extracted by means of a shearing, kneading and grinding device such as an extruder and a colloid mill, or by means of a high speed mixing device such as a stirring-type emulsifier, e.g. a homomixer, the material can be successively treated in a short time. While the extraction takes a long time, namely ten or more hours in conventional methods, the extraction time in the process of the present invention can be remarkably shortened. Further, the material can be extracted under alkaline or acidic conditions, for example in 2-4% sodium hydroxide solution for several hours. The material can be extracted with an alkali solution having the pH value of 10.0 or more and containing alkali and can be added to food instead of, for example, sodium carbonate or potassium hydroxide. The material can be also extracted with an acid and can be added to food instead of sodium hydroxide. Such an acid is a short-chain fatty acid having the pH value of 5 or less. Hydrochloric acid, sulfuric acid, phosphoric acid can be exemplified as inorganic acids, and acetic acid, citric acid, gluconic acid, tartaric acid, lactic acid, fumaric acid, malic acid, propionic acid, oxalic acid and the like can be exemplified as organic acids. In the above compounds, hydrochloric acid, oxalic acid, sulfuric acid, phosphoric acid, acetic acid, propionic acid are preferred, and the most preferable acid is acetic acid.

The stages of neutralization, desalting and concentration are conducted by using an ultrafiltration membrane, an electrodialysis membrane, an ion exchange resin or a reverse osmosis membrane or a combination of these means, and the neutralization of material is conducted during desalting or before desalting. For example, the material is desalted by the method of an ultrafiltration membrane which is able to cut the substance having molecular weight millions or less, preferably a hundred thousand or less, and concentrated by the method of a reverse osmosis membrane. The concentration stage is operated with, before or after the neutralization and desalting stage or at the same time.

Morever, the desalted concentrate is treated in a clarification stage by using a micron filter, an adsorbent such as active carbon and an adsorption resin, a centrifugal separator or a combination of these means, and the transparency of the solution can be control led. In this case, it is desirable to use a micron filter 20 having 1.0-0.45 μm hole diameters.

Then, the products can be finally treated in a drying stage by a known method such as spray drying, freeze drying, drum drying and the like. In the drying stage, powder having high water-solubility can be prepared by adding saccharide such as dextrin.

The obtained powder containing the water-soluble hemicellulose can be used medicines, foodstuffs such as yogurt, processed cheese, spread, cookies, sablé, ices, bread and puffed snacks, and a healthy food for constipation.

According to the present invention, the physiological effect of the food hemicellulose ingredients derived from grain can be expected. Namely, the hemicellulose is fermented well by Bifidobacterium in intestines and the cholesterol metabolism can be improved by another mechanism than that of the prevention of cholesterol absorption in small intestine.

The merit of the present invention is that the mass-produced water-soluble hemicelluloses can be obtained by using the above series of steps. Whereby water-soluble hemicelluloses contained in rice bran, wheat bran or grain husk can be efficiently extracted and separated, and powder having high water-solublity can be prepared. The water-soluble powder separated from food fibers can be broadly utilized as physiologically functional water-soluble hemicelluloses in industrial fields of medicine, food such as milk powder, margarine, cheese and the like.

DESCRIPTION OF THE PREFERRED EMBODIMENTS

The following Examples illustrate the present invention more specifically.

EXAMPLE 1

To ten kg of defatted rice bran of raw material, 50 liters of hot water of about 80° C. and 100 g of thermostable amylase (trade name: Termamyl 120 L, Novo Industry Japan Company) were added and mixed with stirring by using a homomixer. Gelatinized starch isolated in the water solution was filtered to remove and the starch-free residue was collected. In Table 1, the constituents of the rice bran of raw material and the rice bran after removing the starch are tabulated.

TABLE 1

|  | Rice bran of raw material | (%) Rice bran after removing the starch |
|---|---|---|
| Moisture | 5.09 | 3.94 |
| Crude protein | 20.44 | 24.95 |
| Ash | 14.14 | 14.57 |
| Total dietary fiber* (TDF) | 31.37 | 42.18 |

*Analyzed by a Prosky method.

As shown in Table 1, the content of total dietary fiber is not decreased by the treatment for removing starch, and it is observed that the concentration of the dietary fibers is increased.

Then, 25 liters of 2% sodium hydroxide solution was added to 5 kg of rice bran after removing the starch, and the mixture was stirred and extracted for four hours at 80° C. in a tank. The extracted solution was separated into a solid phase and a liquid phase with a decanter which is operated by centrifugal force of 5,000 r.p.m., and the obtained liquid phase was concentrated to five liters by using a reverse osmosis membrane (trade name: NTR 7450, produced by Nitto Denko Company) The concentrated liquid was desalted with an ultrafiltration membrane which was able to cut the substance having a hundred thousand or less of molecular weight (trade name: GR40PP, produced by DDS Company). The water which was lost in the desalting was supplemented with a 0.1 N aqueous hydrochloric acid solution, and the neutralization and the desalting was simultaneously conducted.

Furthermore, after the concentrated liquid was passed through a column of active carbon, the liquid was passed through a 45 μm micronfilter to remove proteins causing a turbidity. The liquid was then spray-dried and about 400 g of gray powder was obtained. The powder was redissolved in water to obtain a 1% aqueous solution, and a brownish transparent solution was obtained. The solution was tastless and had little viscosity.

Table 2 shows the analytical values of the constituents of the hemicellulose prepared by Example 1.

TABLE 2

|  | Rice bran hemicellulose |
|---|---|
| Cellulose | 0.2 |
| Noncellulosic polysaccharides | 61.3 |
| Glucose | 4.3 |
| Arabinose | 26.3 |
| Xylose | 24.7 |
| Galactose | 0.3 |
| Mannose | 0 |
| Uronic acid | 5.7 |
| Lignin | 1.8 |
| Total nitrogen | 4.5 |
| Ash | 7.1 |

(Values are expressed as % of dry matter.)

EXAMPLE 2

Rice bran from which starch was removed by using the same method as described in Example 1 was dried in airing. The repowdered rice bran was used as raw material. The raw material was successively extracted with a twin-screw extruder under the conditions of a material feed rate of 9.5 kg/h, a screw speed of 200 r.p.m., a pressure of 0.4 MPa, and a temperature of 85° C. Two kinds of liquid which were extracted by adding 0.5 N sodium hydroxide and by adding 0.5 N acetic acid, respectively, at a rate of 23.9 1/h were prepared.

Each extracted material was a slurry. Hot water was added to the extracted material to dissolve the extracted hemicellulose. Then, the hemicellulose solution was neutralized, desalted, concentrated, clarified and dried in a similar manner as in Example 1, and hemicellulose powder was obtained. When 100 g of rice bran was extracted with acetic acid, about three grams of the hemicellulose, was obtained, while 100 g of rice bran was extracted with sodium hydroxide, 4.5 g of the hemicellulose was obtained. Accordingly, a good result was obtained in the case of sodium hydroxide However, since the solution was browned by using sodium hydroxide, the kind of solvents should be determined according to food to be used.

EXAMPLE 3

Rice bran was treated by the starch removing stage, the extraction stage, and the neutralization and desalting stage of the present invention to obtain a hemicellulose solution. The solid amount of dextrin (DE10) equal to that of the obtained hemicellulose was added to dissolve to the hemicellulose solution The mixture was spray-dried to obtain powder by using the same method as described in Example 1.

The following method was used for examining the solubility of the sample powder. The hemicellulose powder obtained in Example 1 was used as a control.

Three grams of each sample was added to 100 ml of hot water (60° C.) contained in 200 ml of a beaker, the mixture was stirred with a spoon 60 times (two revolutions per second), and the insolubility of each sample was distinguished by the amounts of insoluble substance and undissolved lumps. As the result, the insoluble substance and undissolved lumps in the control were observed in large quantities, while these were little observed in the sample of this Example.

EXAMPLE 4

Rice bran from which starch was removed by using the same method as described in Example 1 was dried in airing. The repowdered rice bran was used as raw material. The raw material was successively extracted by using a twin-screw extruder under the conditions of a material feed rate of 9.5 kg/h, a screw speed of 200 r.p.m., a pressure of 0.4 MPa and a temperature of 85° C. The liquid which was extracted by adding 0.5 N acetic acid at a rate of 23.9 1/h was prepared.

Hot water was added to the extracted slurry to dissolve hemicelluloses. The mixture was neutralized with 1 N sodium hydroxide and separated into a solid phase and a liquid phase by means of a decanter which was operated by the centrifugal force of 5,000 r.p.m. and the obtained liquid phase was concentrated and desalted by using an ultrafiltration membrane of cut-off molecular weight 100,000 or less (trade name: GR40PP, produced by DDS Company).

Then, the desalted aqueous solution was spray dried to obtain the hemicellulose B fraction powder of rice bran about 300 g.

The following materials containing the obtained powder were combined and sterilized at 100° C. for 30 minutes and then apple juice was prepared.

| Apple Juice (1/5 concentration) | 1,000 g |
|---|---|
| Isomerized sugar | 1,000 g |
| Citric acid | 100 g |
| Water | 16,600 g |
| Water-soluble hemicellulose B fraction powder | 200 g |

As regards the flavor and the taste, the obtained apple juice was equal to a drink having no food fibers.

EXAMPLE 5

The following materials containing the water-soluble hemicellulose B fraction powder which was obtained in Example 4 was combined and sterilized at 100° C. for 30 minutes and then a plain drink was prepared.

| Plain syrup | 2,000 g |
|---|---|
| Isomerized sugar | 1,800 g |
| Citric acid | 100 g |
| Water | 15,900 g |
| Water-soluble hemicellulose B fraction powder | 200 g |

As regards the flavor and the taste, the obtained plain drink was equal to a drink having no food fibers.

COMPARATIVE EXAMPLE 1

The same ingredients as in Example 4 were used except that guar gum 200 g was used instead of the water-soluble hemicellulose B fraction powder.

COMPARATIVE EXAMPLE 2

The same ingredients as in Example 5 were used except that carrageenan 200 g was used instead of the water-soluble hemicellulose B fraction powder.

Texture of the drinks which were obtained by the above Examples 4 and 5 and Comparative Examples 1 and 2 was estimated. As the result, both drinks which were obtained by Comparative Examples 1 and 2 had high viscosity and the texture was poor. On the other hand, the drinks obtained by Examples 4 and 5 were flavorful and had good taste.

EXAMPLE 6

To ten kg of defatted rice bran of raw material, 50 liters of hot water of about 80° C. and 100 g of thermostable amylase (trade name: Termamyl 120 L, Novo Industry Japan Company) were added and mixed with a homomixer. Gelatinized starch isolated in the water solution was filtered to remove and the residue was collected by separating into a solid phase and a liquid phase by means of filtration. Then, 25 liters of 2% sodium hydroxide solution was added to five kg of this residue, and the mixture was stirred and extracted for two hours at 80° C. in a tank. The extracted solution was neutralized with 36% hydrochloric acid solution. The precipitated hemicellulose A fraction, the precipitated protein and the extracted residue were separated into a solid phase and a liquid phase by means of a decanter which was operated by centrifugal force of 5,000 r.p.m. and a clarifier of 7,200 r.p.m., and the liquid phase was concentrated and desalted by the method of an ultrafiltration membrane which was able to cut the substance having a hundred thousand or less of molecular weight (trade name: GR40PP, produced by DDS Company) to obtain the water-soluble hemicellulose B fraction.

Then, the obtained water solution was spray-dried and about 400 g of the water-soluble hemicellulose B fraction powder was obtained.

The obtained powder 400 g was dissolved in 2.0 kg of water at 60° C., the solution was added to 25 kg of fresh milk and the mixture was stirred The mixture was sterilized at 130° C. for two seconds, concentrated and spray dried. 3kg of milk powder containing 10.8% by weight of the hemicellulose B fraction powder of rice bran was obtained. Then, the obtained milk powder was made into granules having grain size of 200-350 μm by using a fluid tank granulator.

EXAMPLE 7

Water-soluble hemicellulose B fraction powder was obtained by using the same method as in Example 6 except that the raw material was changed to corn husk.

The obtained powder was dissolved in 2.0 kg of water at 60° C. The solution was sprayed by using a nozzle for two fluids on 12.5 kg of skimmed milk powder placed in a fluid tank granulator with stirring, and coated granules were obtained. Then, the obtained granules were dried Granulated milk powder having grain size of 250-400 μm and containing the water-soluble hemicellulose B fraction derived from corn husk was obtained The obtained granulated powder skimmed milk contained 2.9% by weight of the water-soluble hemicellulose B fraction. cl COMPARATIVE EXAMPLE 3

400 g of guar gum was dissolved in 20.0 kg of warmed water. The solution was added to 25 kg of fresh milk with stirring. The milk solution was sterilized at 130° C. for two seconds, concentrated and dried 3 kg of milk powder containing 10.6% by weight of the guar gum was obtained. Then, the obtained milk powder was made into granules having grain size of 200-350 μm by using a fluid tank granulator. Taste and solubility of each milk powder obtained in Examples 6 and 7 and Comparative Example 3 were estimated. The results are shown in Table 3.

TABLE 3

|  | Taste | Solubility | Total |
|---|---|---|---|
| Example 6 | Excellent, creamy and good | No solids or no insolubles | Good |
| Example 7 | Excellent and good | No solids or no insolubles | Good |
| Comparative Example 3 | No excellent and a little good | Solids and insolubles | No good |

The above taste and solubility were determined by the following method.

1) 10g of a sample was placed in 200 ml of a beaker and 90 ml of warmed water was added. The mixture was dissolved after 60 revolutions of stirring
2) After the dissolution, the solubility was determined by the appeared solids and insolubles.
3) The taste of the solution was estimated.

EXAMPLE 8

157 kg of water was added to 24 kg of skimmed milk powder and the mixture was stirred well. After dissolving, the solution was placed in a nominal 360 liter tank having a jacket and sterilized at 95° C. for ten minutes by using steam indirect heating Then, the tank was cooled to 42° C. in cooling water. Culture of mixed germ MRC-32 of *Lactobacillus bulgaricus and Streptococcus thermophilus* was inoculated in the solution and the solution was fermented at 42° C. for five hours. While stirring the fermented solution, chilled water was circulated in the jacket to cool down the solution to 10° C.

The other hand, 40 kg of isomerized sugar (S-30 manufactured by Harano Sangyo Company) and 58 kg of water were added to 1 kg of pectin (X-92 manufactured by Unipectin Company) and 1.43 kg (equivalent to 0.5 parts by weight per total) of hemicellulose. The mixture was dissolved with stirring, sterilized at 90° C. for ten minutes and then cooled to 10° C.

The cooled solution containing the pectin, the isomerized sugar and the hemicellulose was added to the above cooled fermented solution with stirring. The stirred solution was homogenized by using a high-pressure homogenizer (manufactured by Sanwa Nyuki Company). The homogenized solution was charged in 550 ml of paper packages for mild and stored in constant temperature room at 10° C. for two weeks.

After two weeks, the solution was tested. As shown in Table 4, the same results as a control no adding hemicellulose were obtained. The texture and the structure satisfied the demand of fluid-type yogurt.

TABLE 4

|  | Adding hemicellulose | No adding hemicellulose |
|---|---|---|
| Just after producing |  |  |
| pH | 4.25 | 4.24 |
| Viscosity | 15.0 cp | 15.5 cp |
| Texture | 9 | 9 |
| Seven days after storage |  |  |
| pH | 4.15 | 4.15 |
| Viscosity | 15.0 cp | 15.0 cp |
| Texture | 9 | 9 |
| 14 days after storage |  |  |
| pH | 4.07 | 4.06 |
| Viscosity | 14.5 cp | 15.0 cp |

TABLE 4-continued

| | Adding hemicellulose | No adding hemicellulose |
|---|---|---|
| Texture | 8 | 8 |

*Viscosity was determined with a B type viscometer (No. 1 rotor).

The taste was judged using a rating of 1 to 10, 10 being the best.

EXAMPLE 9

34 kg of Cheddar cheese and 20 kg of Gouda cheese were pulverized and mixed 1.1 kg of a melted salt (a complex with 80% sodium polyphosphate and 20% sodium diphosphate) and 1.1 kg of hemicellulose were added to the mixture, and the obtained mixture was heated at 85°–90° C. in a Stefan cutter (750 rpm) and dissolved. The obtained processed cheese containing the hemicellulose was packed in packages and cooled. As regards the taste, the structure and the flavor, the obtained cheese was equal to conventional cheese having no hemicellulose.

EXAMPLE 10

To an oil phase 82% by weight comprised of a mixed oil (containing 20 parts by weight of bean oil hydrogenated a little water (melting point:40° C.), 20 parts by weight of palm oil and 42.5 parts by weight of corn oil, melting point:32° C.) of bean oil, palm oil, rapeseed oil and corn oil or processed oil thereof and oil soluble material such as an emulsifying agent and the like, a water phase 16.5% by weight (containing common salt) having 1.0% by weight of hemicellulose were added. By using a conventional method of producing margarine, the oil phase and the water phase were mixed and emulsified. The emulsion was cooled, solidified and milled with a heat transfer of a surface scraping type like a combinator, and W/O type margarine was obtained.

In view of the latest diet intention, the rate of the oil phase was adjusted to less than 40.0% by weight. More than 60.0% by weight of the water phase containing 1.0% by weight of the hemicellulose of the present invention and the above oil phase were mixed and treated by the above method and W/O type fat spread was obtained As regards the taste, the obtained spread was equal to conventional margarine. 50 mg - 2 g of the hemicellulose per meal (10 g of margarine) could be eaten.

EXAMPLE 11

Cookies (a sheet type)

A small amount of ground vanilla was added to the mixture of 150 parts by weight of butter, 200 parts by weight of granulated sugar and 3 parts by weight of common salt with stirring. 50 parts by weight of whipped egg was added and stirred to form paste. A mixture of 4 parts by weight of sifted baking soda, 450 parts by weight of soft flour and 50 parts by weight of hemicellulose was slowly added to the paste with stirring. The obtained material was placed in a refrigerator for 20 minutes, the cooled material was spread so as to obtain a sheet having a thickness of 3-4 mm on a support powdering a small amount of flour and the obtained sheet was formed with various molds. The formed material was placed on a shallow pan on which a baking sheet was spread and baked in an oven at 180° C. for about 15 minutes. If necessary, a suitable amount of finely chopped nuts (for example, almonds, peanuts or walnuts), raisins or chocolate chips can be added

EXAMPLE 12

Sablé (a squeezing out type)

100 parts by weight of butter and 50 parts by weight of shortening were blended, and then 100 parts by weight of sucrose was added with stirring A mixture of 40 parts by weight of whipped eggs and 15 parts by weight of egg yolks was divided into three portions and the mixture was added for three times to the blend. The blend was stirred to form paste. 230 parts by weight of sifted soft flour and 20 parts by weight of hemicellulose were added and lightly mixed to obtain a mass. The mass was squeezed out on a shallow pan on which a baking sheet was spread and baked in an oven at 200° C. for about 15 minutes.

EXAMPLE 13

Using raw materials which were combined as shown in Table 5, ice in cups was prepared.

TABLE 5

| | (% by weight) |
|---|---|
| Raw cream (47%) | 20.0 |
| Sweetened skimmed condensed milk | 10.0 |
| Skimmed milk powder | 7.0 |
| Granulated sugar | 4.0 |
| Glucose fractose liquid sugar (13 × 75) | 2.0 |
| Powdered millet jelly (DE30) | 5.0 |
| Glycerin fatty acid ester | 0.2 |
| Stabilizer (note) | 0.25 |
| Hemicellulose | 1.0 |
| Water | 50.35 |
| Vanilla extract | 0.2 |

Note: Stabilizer for ice cream containing locust bean gum, guar gum and carrageenan in a ratio of 5:4:1.

After powders of the granulated sugar, skimmed milk powder, powdered millet jelly, glycerin fatty acid ester and stabilizer were mixed well, the mixture was dispersed in water by using a homomixer (manufactured by Tokushu Kika Kogyo Company). Raw cream, sweetened skimmed condensed milk, gluose fractose liquid sugar were added to them. The mixture was heated to 85° C. with stirring, maintained for one minute and sterilized, then homogenized at a pressure of 150 kg/cm² by using a homogenizer (manufactured by Sanwa Machine), and immediately cooled to 5° C. Vanilla extract was added. After aging, the mixture was foamed to overrun about 60% and freezed by using a soft cream freezer (manufactured by Mitsubishi Heavy Industries, Ltd.), and filled in cups and then hardened and stored at −30° C.

The hardened ice was thawed out at room temperature for several minutes. The ice had good thickness and taste. Moreover, it had the shape retention at room temperature for ten and more minutes.

EXAMPLE 14

Using the following conditions, bread was produced by a sponge dough method.

| | Test class | Control class |
|---|---|---|
| (sponge dough ingredients) | | |
| First hard flour | 700 g | 700 g |
| Yeast (compressed) | 25 g | 25 g |
| Water | 450 g | 450 g |
| Mixer: | two minutes at a low speed, one minute at a | |

-continued

|  | Test class | Control class |
|---|---|---|
|  | middle speed | |
|  | kneading temperature 26° C. | |
| Fermentation: | two hours and a half at 28 ± 1° C. | |
| (Kneading ingredients) | | |
| First hard flour | 250 g | 300 g |
| Hemicellulose* | 50 g | — |
| Salt | 21 g | 21 g |
| Granulated sugar | 50 g | 50 g |
| Skimmed milk powder | 20 g | 20 g |
| Shortening | 40 g | 40 g |
| Water | 220 g | 206 g |
| Mixing and kneading: | two minutes at a low speed, five minutes at a high speed, after adding the shortening, two minutes at a low speed and three minutes at a high speed | |
| Kneading temperature: | 28° C. | |
| Floor time: | 30 minutes at 28 ± 1° C. | |
| Division: | 450 g | |
| Bench: | 20 minutes | |
| Forming: | mountain-shaped | |
| Drier: | 85% RH. for 60 minutes at 38 ± 1° C. | |
| Baking: | 23 minutes at 210 ± 5° C. | |
| Product: | | |
| Volume | 2140 ml | 2250 ml |
| Pore Rate | 5.49 ml/g | 7.55 ml/g |

*Hemicellulose was added and mixed to wheat flour.

As regards the flavor and the taste, the produced bread was equal to the bread of control class.

EXAMPLE 15

Application for puffed snacks

As foodstuffs of Ready To Eat Cereal (R.T.E), puffed snacks which were obtained by extrusion cooking are shown.

| | Ingredients | |
|---|---|---|
|  | Test goods | Control goods |
| Corn flour | 21.57 | 55.22 |
| Wheat flour | 35.00 | — |
| Corn bran* | — | 27.0 |
| Hemicellulose | 20.7 | — |
| Skimmed milk powder | 10.0 | 7.0 |
| Granulated sugar | 4.5 | 4.5 |
| Sodium ferric citrate | 0.3 | 0.3 |
| Calcium carbonate | 2.5 | 2.5 |
| Natural calcium agent | 1.4 | 1.4 |
| Vitamin C | 0.13 | 0.13 |
| Table salt | 0.6 | 0.6 |
| Palm oil | 3.0 | 1.0 |
| Flavors | 0.30 | 0.35 |

*Corn bran was used for food fiber materials insoluble in water.

The above combined powder was treated by a twin-screw extruder under the following conditions.

| Mass feed rate | 24 kg/h |
|---|---|
| Feed moisture content | 4 kg/h |
| Screw speed | 200 rpm |
| Maximum temperature | 150° C. |
| Maximum pressure | 0.5 MPa |

Both treated products were eaten crisp and tasted good.

EXAMPLE 16

Medicine for improving constipation containing tablet type hemicellulose

Using the hemicellulose which was prepared by the process of the present invention, tablets for improving constipation were prepared by blending the following ingredients.

| Ingredients | Blending (wt %) |
|---|---|
| Hemicellulose | 55.0 |
| Cornstarch | 40.8 |
| Crystallized cellulose | 2.5 |
| Calcium Carboxymethyl Cellulose | 1.7 |

In accordance with the above blending, 2200 g of hemicellulose, 1632 g of cornstarch, 100 g of crystalline cellulose and 68 g of calcium carboxymethyl cellulose were mixed with a kneader and then kneaded by adding dropwise 500 ml of water. The kneaded mixture was granulated with a single axis oscillator on which a 20 mesh screen was set and dried with a fluidized bed dryer. The dried product was ground with a flash mill to obtain uniformed particles. The particles and 80 g of sucrose fatty ester as a smoothing agent were mixed with a V type blender. The mixture was tableted with a tableting machine on which a pestle having a diameter of 11 mm was set. Tablets having an average weight of 0.35 g were obtained.

EXAMPLE 17

Granular foodstuffs containing hemicellulose

Using the hemicellulose prepared by the process of the present invention, granular foodstuffs were prepared by blending the following ingredients.

| Ingredients | Blending (wt %) |
|---|---|
| Hemicellulose | 30.0 |
| Powdered sugar | 35.0 |
| Lactose | 25.0 |
| Cornstarch | 9.5 |
| Flavors | 0.5 |

In accordance with the above blending, 1200 g of hemicellulose, 1400 g of powdered sugar, 1000 g of lactose, 300 g of cornstarch and 20 g of flavors were mixed with a kneader and then kneaded by adding dropwise 350 ml of water. The kneaded mixture was granulated with an extruder granulator of a cylinder type equipping screen meshes having a diameter of 11 mm and dried with a fluidized bed dryer. The dried particles were uniformed with a flash mill and sieved to obtain 3400 g of a product.

As regards the taste and the flavor, the obtained product was good. On the other hand, a product containing conventional food-fibers was disagreeable to the taste and the flavor.

We claim:

1. A process of producing a water-soluble hemicellulose comprising the steps of:
   a) adding hot water and thermostable amylase to a raw material selected from the group consisting of rice bran, wheat bran and grain husk to remove starch contained in the raw material, whereby the amylase breaks down the raw material and the starch becomes dissolved in the water and thereby forms a gelatinized starch solution;

b) removing the gelatinized starch solution of step a), wherein the amylase remaining in the gelatinized solution breaks down the starch into dextrin or smaller carbohydrates;

c) separating the gelatinized solution of step b) into solid and liquid phases; wherein the solid phase contains a water-soluble hemicellulose, cellulose, lignin, protein and minerals, and the liquid phase contains the starch and smaller carbohydrates which are not broken down;

d) dissolving the solid phase of step c) with a solvent having an acidic pH of at most 5 or an alkaline pH of at least 10 which forms a second solid and liquid phase, wherein the liquid phase contains the water-soluble hemicellulose;

e) separating the liquid phase of step d) from the solid phase; and f) neutralizing and desalting the separated liquid phase of step e) to obtain the water-soluble hemicellulose.

2. A process as claimed in claim 1, wherein a stirring-type emulsifier or a colloid mill is used in the starch removing stage.

3. A process as claimed in claim 1, wherein the extraction is conducted by means of an extruder, a colloid mill, a stirring-type emulsifier or one of these combinations.

4. A process as claimed in claim 1, wherein the neutralization and desalting is conducted by the method of at least one selected from the group of an ultrafiltration membrane, an electrodicalysis membrane, an ion exchange resin, a reverse osmosis membrane and one of these combinations, and the material is neutralized during desalting or before desalting.

5. A process as claimed in claim 1 wherein concentration conducted with, after or before the neutralization and desalting stage or at the same time.

6. A process as claimed in claim 5 wherein an ultrafiltration membrane or a reverse osmosis membrane is used in the concentration stage.

7. A process as claimed in claim 1, further comprising a drying stag e in which the material is dried in the presence of saccharide.

8. A water-soluble hemicellulose which is obtained a process as claimed in claim 1.

* * * * *